(12) United States Patent
Izumizawa et al.

(10) Patent No.: US 8,148,079 B2
(45) Date of Patent: Apr. 3, 2012

(54) METHOD OF PRODUCING AMPLIFICATION PRODUCT BY PCR AND USAGE THEREOF

(75) Inventors: Yuji Izumizawa, Kyoto (JP); Satoshi Majima, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 431 days.

(21) Appl. No.: 12/294,304

(22) PCT Filed: Aug. 7, 2007

(86) PCT No.: PCT/JP2007/065460
§ 371 (c)(1),
(2), (4) Date: Sep. 24, 2008

(87) PCT Pub. No.: WO2008/018469
PCT Pub. Date: Feb. 14, 2008

(65) Prior Publication Data
US 2009/0269754 A1 Oct. 29, 2009

(30) Foreign Application Priority Data
Aug. 9, 2006 (JP) ................................ 2006-217199

(51) Int. Cl.
*C12Q 1/68* (2006.01)
*C12P 19/34* (2006.01)
(52) U.S. Cl. ..................................... 435/6.12; 435/91.2
(58) Field of Classification Search ............. 435/6, 91.2, 435/6.12
See application file for complete search history.

(56) References Cited

U.S. PATENT DOCUMENTS

| | | | |
|---|---|---|---|
| 5,501,963 A | | 3/1996 | Burkhardt |
| 2004/0091864 A1* | | 5/2004 | French et al. ..................... 435/6 |
| 2005/0260606 A1 | | 11/2005 | Kermekchiev et al. |
| 2006/0216720 A1* | | 9/2006 | Carvalho et al. .................. 435/6 |

FOREIGN PATENT DOCUMENTS

| | | |
|---|---|---|
| EP | 0 751 226 | 1/1997 |
| JP | 6-277062 A | 10/1994 |
| JP | 9-187277 A | 7/1997 |
| JP | 3727667 B2 | 10/2005 |
| WO | 2005/118772 A1 | 12/2005 |

OTHER PUBLICATIONS

Supplementary European Search Report issued in corresponding European Application No. 07792129.4, European Patent Office, Dec. 22, 2009—8 pages.

Al-Soud, et al., "A sample preparation method which facilitates detection of bacteria in blood cultures by the polymerase chain reaction", Journal of Microbiological Methods, vol. 32, No. 3, pp. 217-224, 1998.
Al-Soud, et al., "Capacity of Nine Thermostable DNA Polymerases to Mediate DNA Amplification in the Presence of PCR-Inhibiting Samples", Applied and Environmental Microbiology, vol. 64, No. 10, pp. 3748-3753, 1998.
Burckhardt, "Amplification of DNA from Whole Blood", PCR Methods and Applications, vol. 3, No. 4, pp. 239-243, 1994.
Wu, et al., "A Simple and Economic Method for Directly Performing PCR on Washed Blood Cells or Whole Blood", Clinical Chemistry, vol. 39, No. 4, p. 737, 1993.
Panaccio, et al., "FoLT PCR: A Simple PCR Protocol for Amplifying DNA Directly from Whole Blood", Biotechniques, vol. 14, No. 2, pp. 238-240, 242 and 243, 1993.
International Search Report of PCT/JP2007/065460, dated Oct. 23, 2007.
Mercier et al. "Direct PCR from whole blood, without DNA extraction." Nucleic Acids Research, vol. 18(19), 1990, p. 5908.
Panaccio et al. "PCR based diagnosis in the presence of 8% (v/v) blood." Nucleic Acids Research, vol. 19(5), 1991, p. 1151.
Pääbo et al. "Mitochondrial DNA Sequences from a 7000-year old brain." Nucleic Acids Research, vol. 16(20), 1998, pp. 9775-9787.
Al-Soud et al. "Purification and Characterization of PCR-Inhibitory Components in Blood Cells." Journal of Clinical Microbiology, vol. 39(2), 2001, pp. 485-493.
Decision of Rejection dated Feb. 28, 2011, Korean Patent Application No. 10-2008-7012967 with partial English translation.
Al-Soud et al., Effects of Amplification Facilitators on Diagnostic PCR in the Presence of Blood, Feces, and Meat. J. Clin. Microbiol. (2000) 38:4463-4470.

\* cited by examiner

*Primary Examiner* — Kenneth R. Horlick
*Assistant Examiner* — Joyce Tung
(74) *Attorney, Agent, or Firm* — Morgan, Lewis & Bockius LLP

(57) ABSTRACT

A method of producing a PCR amplification product is provided that suppresses an effect of precipitate, turbidity, or the like derived from a whole blood sample on a detection in the detection of an amplified nucleic acid by an optical unit. The amplification product complementary to a target nucleic acid in the whole blood sample is produced by PCR in a condition where a ratio of the whole blood sample in a PCR reaction solution is in the range of 0.1 to 0.9% by volume or 0.01 to 1.8 g/L in term of hemoglobin content. When the PCR is carried out with such conditions, even with an untreated whole blood sample, a monitoring of the amplification product by the optical unit can be done while suppressing the effect of the precipitate or the turbidity.

26 Claims, 3 Drawing Sheets

SEQUENCE LISTING

<160> NUMBER OF SEQ ID NOS: 5

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
gaagagccaa ggacaggtac                                              20

<210> SEQ ID NO 2
<211> LENGTH: 21
<212> TYPE: DNA
<213> ORGANISM: Artificial
<220> FEATURE:
<223> OTHER INFORMATION: primer

<400> SEQUENCE: 2
ggaaaataga ccaataggca g                                            21

<210> SEQ ID NO 3
<211> LENGTH: 18
<212> TYPE: DNA
<213> ORGANISM: Artificial
<220> FEATURE:
<223> OTHER INFORMATION: primer

<400> SEQUENCE: 3
cacatgtgca acgcagcg                                                18

<210> SEQ ID NO 4
<211> LENGTH: 24
<212> TYPE: DNA
<213> ORGANISM: Artificial
<220> FEATURE:
<223> OTHER INFORMATION: primer

<400> SEQUENCE: 4
ctcttgccat atgtattgga tccc                                         24

<210> SEQ ID NO 5
<211> LENGTH: 34
<212> TYPE: DNA
<213> ORGANISM: Artificial
<220> FEATURE:
<223> OTHER INFORMATION: probe

<400> SEQUENCE: 5
ttcattccag caacaacttt ggtgccattc tctc                              34

METHOD OF PRODUCING AMPLIFICATION PRODUCT BY PCR AND USAGE THEREOF

TECHNICAL FIELD

The present invention relates to a method of producing an amplification product by PCR and a method of analyzing the amplification product and a target nucleic acid by using the same.

BACKGROUND ART

In various fields such as a clinical field, a pathologic field, etc., a polymerase chain reaction (PCR) method is used widely for the purpose of a gene expression analysis, a gene function analysis, genetic diagnoses, and the like. The PCR method generally includes three steps:
1) denaturing DNA (dissociation from double-stranded DNA into single-stranded DNA) by a heat treatment;
2) annealing a primer to single-stranded DNA template; and
3) extending the primer by DNA polymerase as a cycle and, by repeating the cycle, amplifies DNA complementary to a target nucleic acid in a sample.

However, when a biological sample, especially a whole blood sample, is subjected to PCR, because of the heat treatment for the DNA denaturation, saccharide and protein contained in the sample are denatured and an insoluble precipitate, turbidity, or the like, is generated. The generation of such precipitate, or the like does not become a big problem when the presence or absence of the amplification product is confirmed by electrophoresis, for example. However, when the presence or absence of the amplification product is confirmed by an optical unit, because the precipitate or the turbidity blocks an irradiated light, there is a problem that accurate measurements cannot be obtained. Especially, with a method of monitoring a preparation process of the amplification product with time in PCR (what is called, a real time PCR method), for example, quantitative analysis of the amplification product per cycle and a count of the number of the cycles when the amplification product reaches a specified quantity (threshold value) can be performed. Further, on the basis of those information, quantitative analysis of the target nucleic acid in the biological sample also can be performed. Therefore, a high emphasis is placed on a realization of an accurate measurement by the optical unit.

In order to solve such problem, conventionally, methods are taken in which the biological sample is purified preliminarily in advance of the use as a PCR sample (pretreatment) and in which a PCR reaction solution is purified after a reaction (aftertreatment). Examples of the pretreatment of the biological sample include methods: in which the heat treatment is preliminarily applied to the biological sample and the generated precipitate or the like is removed and then an obtained supernatant is used as the PCR sample; and in which a causative substance of the precipitate, the turbidity, or the like is removed preliminarily from the biological sample. Further, an example of the aftertreatment of the PCR reaction solution includes a method in which the precipitate or the like generated after the PCR reaction is removed in advance of a detection of the amplification product.

On the other hand, with the PCR using the biological sample, from the perspective of ease and swiftness of an operation, it is desired that the biological sample is used as it is without applying the pretreatment such as the purification. In this state, it is reported that the ratio of the whole blood sample in the PCR reaction solution is in a range of about 1 to 10% by volume (Patent Document 1, Non-Patent Documents 1 and 2).

However, as described above, when the detection of the amplification product is carried out by the optical unit with a former method, the pretreatment (a purification treatment) of the biological sample is required. Further, with a latter method, although the biological sample can be used as it is, because a removal of the precipitate after completion of the reaction is required, the operation becomes as complicated as the former method. Moreover, there is a problem that the analysis can be performed only after the completion of the reaction. In other words, although the amplification product finally obtained can be analyzed, it is difficult to monitor the preparation process of the amplification product with time by the optical unit. Further, with respect to the biological sample such as the whole blood sample, without applying the pretreatment, there is a problem that the PCR reaction may be hindered due to components contained therein (Non-Patent Documents 3 and 4).

[Patent Document 1] JP3727667B
[Non-Patent Document 1] Nucleic Acids Research, Vol. 18, No. 19, 5908 (1990)
[Non-Patent Document 2] Nucleic Acids Research, Vol. 19, No. 5, 1151 (1991)
[Non-Patent Document 3] Nucleic Acids Research, Vol. 16, No. 20, 9775-9787 (1998)
[Non-Patent Document 4] Journal of Clinical Microbiology, Vol. 39, No. 2. p 485-493 (2001)

DISCLOSURE OF INVENTION

Hence, the present invention is intended to provide a method of producing an amplification product by PCR that can suppress an effect of the precipitate, the turbidity, or the like derived from a whole blood sample on a detection in the detection of an amplified nucleic acid by an optical unit. More specifically, the present invention relates to a method of producing a PCR amplification product that can suppress the effect of the precipitate, the turbidity, or the like on the detection without requiring, for example, a purification of the whole blood sample in advance of a PCR reaction (pretreatment), or a purification of a PCR reaction solution after the PCR reaction (aftertreatment). Further, the present invention is intended to provide a method of performing qualitative or quantitative analysis of the amplification product by the optical unit while suppressing the effect of the precipitate, the turbidity, or the like, and to provide an analysis of a target nucleic acid in the whole blood sample.

In order to achieve the aforementioned object, the method of producing the amplification product of the present invention is a method of producing an amplification product complementary to the target nucleic acid in the whole blood sample by PCR, wherein the ratio of the whole blood sample in a PCR reaction solution is in the range of about 0.01 to 0.9% by volume. Further, the ratio of the whole blood sample in the PCR reaction solution may be in the range of about 0.01 to 1.8 g/L in term of hemoglobin content.

The method of analyzing the amplification product of the present invention is a method of performing qualitative or quantitative analysis of the amplification product prepared by PCR, wherein the method includes:

(A) a process of preparing the amplification product complementary to the target nucleic acid in the whole blood sample by the method of producing the amplification product of the present invention; and (B) a process of detecting the amplification product by the optical means.

The method of analyzing the target nucleic acid of the present invention is a method of performing quantitative analysis of the target nucleic acid contained in the sample, wherein the sample is the whole blood sample, and wherein the method includes:

(A) a process of preparing the amplification product complementary to the target nucleic acid in the whole blood sample by the method of producing the amplification product of the present invention;

(B) a process of performing quantitative analysis of the amplification product by detecting the amplification product by the optical unit; and (C) a process of performing quantitative analysis of the target nucleic acid in the whole blood sample that comprises confirming the number of cycles of PCR where the amplification product reaches a specified quantity.

According to the method of producing the amplification product of the present invention, by only setting the ratio of the whole blood sample in the PCR reaction solution in the aforementioned range, without applying the pretreatment of the whole blood sample or the aftertreatment of the PCR reaction solution as conventional, the amplification product can be obtained while suppressing the effect of the turbidity, the precipitate, or the like on the detection. Further, with respect to the aforementioned ratio, it is confirmed that the target nucleic acid can be amplified by PCR if it exists in the whole blood sample, and sufficient amplification efficiency can be ensured. Further, according to the present invention, because the effect of the turbidity, the precipitate, or the like can be suppressed, the amplification product can be detected not only by the electrophoresis as conventionally but also by the optical unit. Moreover, because the amplification product can be detected by the optical unit, monitoring of the amplification product in the preparation process with time can be realized, which was impossible by the electrophoresis. Therefore, according to the present invention, even when an untreated whole blood sample not subjected to the purification treatment is used, for example, not only qualitative or quantitative analysis of the amplification product but also qualitative or quantitative analysis of the target nucleic acid in the whole blood sample can be performed. In the detection of the amplification product, in a case where the problem of the turbidity, the precipitate, or the like occurs as described above (namely, in a case of the detection by the optical unit), because the use of the untreated whole blood sample itself is not conventionally attempted as described below, as well as the configuration of the present invention, the problem to be solved by the invention has novelty.

BEST MODE FOR CARRYING OUT THE INVENTION

Amplification Product Producing Method

Figure 1:
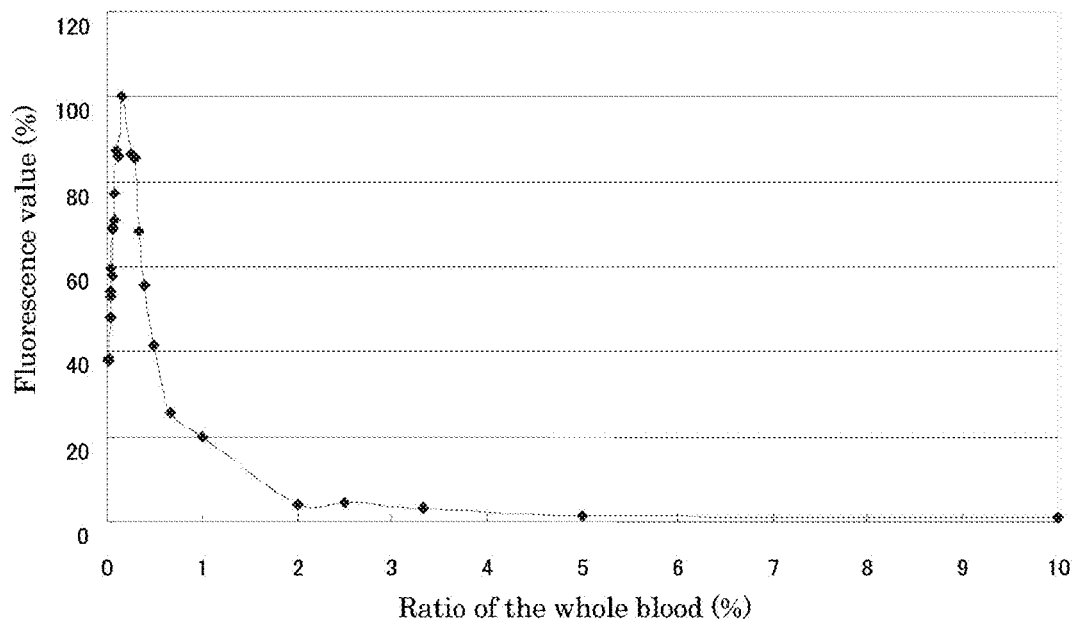
FIG. 1 is a graph indicating the relationships between a ratio of whole blood in a PCR reaction solution and a fluorescence value corresponding to a PCR amplification product in an Example 1 of the present invention.

A method of producing an amplification product according to the present invention is, as mentioned above, a method of producing an amplification product complementary to a target nucleic acid in a whole blood sample by PCR, wherein the ratio of the whole blood sample in a PCR reaction solution is in the range of about 0.01 to 0.9% by volume. In the present invention, the ratio of the whole blood sample means the final concentration (% by volume) in the PCR reaction solution.

When the ratio of the whole blood sample exceeds 0.9% by volume, for example, protein or the like in the sample is denatured because of a heat treatment in PCR and the effect of generation of the precipitate or the like in the reaction solution on the detection may not be suppressed sufficiently. Further, when the ratio of the whole blood sample exceeds 0.9% by volume, for example, an inhibition of a PCR reaction due to components in the sample may not be suppressed sufficiently and amplification efficiency may be insufficient. According to the method of producing the amplification product of the present invention, by setting the ratio of the whole blood sample in the aforementioned range, for example, generation of the precipitate or the like under the PCR reaction can be suppressed. In this state, the present invention can be considered a method of suppressing generation of the precipitate, turbidity, or the like. Further, the precipitate or the like is, as described above, a detection inhibitor at the time of detecting the amplification product by the optical unit. For this reason, the present invention also can be said to be a method of suppressing generation of the detection inhibitor.

While the ratio of the whole blood is in the range of 1 to 10% by volume in the aforementioned patent document and non-patent documents, the ratio of the whole blood is reduced to the range of 0.01 to 0.9% by volume in the present invention. Therefore, for example, inhibition of the PCR reaction due to the components in the sample can be reduced and thus the amplification efficiency may be increased.

The lower limit of the ratio of the whole blood sample in the reaction solution is, as described above at least 0.01% by volumes preferably at least 0.02% by volume, more preferably at least 0.05% by volume, and further preferably at least 0.1% by volume. Further, the upper limit of the ratio of the whole blood sample is, as described above 0.9% by volume or lower, preferably 0.8% by volume or lower, more preferably 0.7% by volume or lower, further preferably 0.6% by volume or lower.

Further, in the present invention, the ratio of the whole blood sample in the reaction solution can be expressed not only in a volume ratio as described above but also in a weight ratio of hemoglobin (hereinafter, referred to as "Hb"). In this state, the ratio of the whole blood sample in the reaction solution is in the range of about 0.01 to 1.5 g/L in term of Hb content. The lower limit of Hb content is preferably at least 0.05 g/L and more preferably at least 0.1 g/L. The upper limit of Hb content is preferably 1.5 g/L or lower and more preferably 1 g/L or lower. For example, the ratio of the whole blood sample is preferably in the range of 0.05 to 1.5 g/L and more preferably in the range of 0.1 to g/L. In the reaction, the ratio of the whole blood sample may satisfy both of the volume ratio and the Hb weight ratio however may satisfy only one of the volume ratio and the Hb weight ratio.

The whole blood generally is composed of blood cell (solid component) comprising blood platelet, leukocyte (granulocyte, monocyte, and lymphocyte) and erythrocyte and blood plasma (liquid component). For example, erythrocyte contains Hb, etc. therein and blood plasma contains albumin, globulin, blood coagulation factor, etc. therein. As described above, according to the present invention, for example, a pretreatment, in which the whole blood sample is applied with the heat treatment and supernatant is collected by removing the generated precipitate, or in which saccharide or protein causing the generation of the precipitate is removed, in advance of the start of the PCR reaction is not required. Therefore, the whole blood sample in the present invention generally means the whole blood sample without being subjected to the pretreatment (hereinafter, referred to as an untreated whole blood sample), the pretreatment for removing the components causing the precipitate or removing the generated precipitate A form of the whole blood sample subjected to PCR is not particularly limited and, for example, the whole blood collected from a patient may be used as it is or cryopreserved blood may be used by thawing. Further, the whole blood subjected to PCR may be any one of hemolyzed whole blood, unhemolyzed whole blood, anticoagulant whole blood, and the whole blood containing coagulated fraction, for example.

The target nucleic acid to be amplified by PCR includes, for example, foreign nucleic acid (DNA, RNA), etc. introduced to the whole blood via bacteria, virus, etc. as well as DNA and RNA (mRNA, Total RNA) derived from the whole blood. Further, in response to the presence of these target nucleic acid, for example, necessity of hemolysis of the whole blood sample can be determined.

As a more preferable mode of the present invention, albumin is added to the PCR reaction solution in advance of the start of the PCR reaction. In this manner, when albumin is added, the effect of the precipitate, the turbidity, or the like further can be suppressed and the amplification efficiency can be increased further.

As described above, it is known that the component contained in the biological sample such as the whole blood sample inhibits the PCR reaction. As a method for reducing this reaction inhibition, a technology has been reported in which albumin is added to the PCR reaction solution (Non-Patent Documents 3 and 4). However, it is totally unknown that the effect of the precipitate or the like on the detection can be suppressed further by adding albumin to the PCR reaction solution as indicated in the more preferable mode of the present invention. This fact was found by the inventors of the present invention as a result of their keen study. Particularly, in the present invention, it is required that the ratio of the whole blood sample in the PCR reaction solution is set in the aforementioned range as a precondition to the addition of albumin to the PCR, and the effect of the precipitate or the like on the detection cannot be suppressed by simply adding albumin. In other words, the effect of the precipitate or the like on the detection is suppressed not by simply adding albumin but by setting the ratio of the whole blood sample in the aforementioned range. Further, by adding albumin to the PCR reaction solution to coexist, the effect can be suppressed further.

On the other hand, in the Non-Patent Documents 3 and 4 that disclose the addition of albumin, use of the untreated whole blood sample and the problem of the precipitate or the like under an optical detection as well as the ratio of the whole blood sample are not disclosed at all. Further, with respect to the Patent Document 1 and Non-Patent Document 2 that disclose the whole blood sample, a result has been obtained in which the optical detection is difficult with the ratio of the whole blood sample (at least 1% by volume) disclosed therein because the PCR reaction solution turns into jelly when albumin further is added. More importantly, the present invention is intended to suppress the effect of the precipitate or the like because the present invention is provided in view of realizing the detection of the amplification product by the optical unit. As described above, the optical detection by using the untreated whole blood itself is not conventionally attempted.

The ratio of albumin in the PCR reaction solution is not limited and the lower limit thereof is, for example, at least 0.01% by weight, preferably at least 0.1% by weight, and more preferably at least 0.2% by weight, and the upper limit thereof is, for example, 5% by weight or lower, preferably 2% by weight or lower, more preferably 1% by weight or lower, and further preferably 0.8% by weight or lower. The ratio of albumin in the PCR reaction solution is preferably in the range of 0.01 to 5% by weight, more preferably in the range of 0.1 to 2% by weight, and further preferably in the range of 0.2 to 0.8% by weight. The aforementioned albumin is not particularly limited and examples thereof include bovine serum albumin (BSA), human serum albumin, rat serum albumin, horse serum albumin, etc. One albumin may be used alone or two or more albumins may be used in combination. In the present invention, the ratio of albumin means, for example, the final concentration (% by weight) in the PCR reaction solution.

Further, as a more preferable mode, the present invention includes a process of applying the heat treatment to the whole blood sample in advance of the start of the PCR reaction. In this manner, when the whole blood sample is applied with the heat treatment in advance of the PCR reaction, for example, an amount of an initial template can be increased further and thereby the amplification efficiency can be increased further. Further, for example, even when the turbidity, the precipitate, or the like is generated due to the heat treatment of the whole blood sample, because the effect of the turbidity, or the like is suppressed by setting the ratio of the whole blood in the PCR reaction solution in the aforementioned range at the time of the PCR reaction, the amplification product can be detected by the optical unit and the amplification efficiency can be increased further. Moreover, also in a case of adding albumin as described above, the heat treatment may be applied. For example, the heat treatment may be applied either before or after of the addition of albumin.

In the process of the heat treatment, it is preferable that the whole blood sample is a diluted sample. Use of the diluted sample allows, for example, suppression of the generation of the precipitate, the turbidity, or the like due to the heat treatment for an improvement of the amplification efficiency. The ratio of the whole blood sample in the diluted sample is not particularly limited. However, the ratio of the whole blood sample is, for example, in the range of 0.01 to 90% by volume, preferably in the range of 0.05 to 50% by volume, and more preferably in the range of 0.5 to 5% by volume. In the case of applying the heat treatment, for example, the diluted sample applied with the heat treatment may be added to the PCR reaction solution in such a way that the ratio of the whole blood sample falls within the aforementioned range, or the PCR reaction solution, in which the whole blood sample is added in such a way that the ratio thereof falls within the aforementioned range, may be subjected to the heat treatment in advance of the PCR reaction.

Heating temperature in the process of the heat treatment is not limited however is, for example, at least 80° C., preferably in the range of 80 to 99° C., more preferably in the range of 90 to 99° C., and particularly preferably in the range of 95 to 99° C. Further, treating time is not limited however is, for example, at least 30 seconds, preferably in the range of 30 seconds to 15 minutes, more preferably in the range of 1 minute to 15 minutes, and particularly preferably in the range of 3 minutes to 15 minutes.

Next, the method of producing the amplification product according to the present invention is explained with an example in which the target nucleic acid in the whole blood sample is DNA and the DNA is used as a template of PCR. The characteristic of the present invention is setting the ratio of the whole blood sample in the PCR reaction solution in the aforementioned range and other configurations and conditions are not limited at all.

First, the PCR reaction solution is prepared in such a way that the ratio of the whole blood sample is in the aforementioned range. A method of adding the whole blood sample is not limited as long as the ratio thereof in the PCR reaction solution is in the aforementioned range. For example, the whole blood sample may be added directly to the PCR reaction solution, or the whole blood sample may be diluted preliminarily with water or buffer solution and then added to the PCR reaction solution. When the whole blood sample is diluted preliminarily, the dilution ratio thereof is not limited as long as the final ratio of the whole blood in the PCR reaction solution is in the aforementioned range and is, for example, in the range of 100 to 2000 times, and preferably in the range of 200 to 1000 times. Further, whole volume of the PCR reaction solution is not particularly limited and is, for example, determined suitably according to a device used (e.g., a thermal cycler) and is, normally in the range of 1 to 500 µl, and preferably in the range of 10 to 100 µl.

A composition component in the PCR reaction solution other than the whole blood sample is not particularly limited and the composition component includes conventionally known components and the ratio thereof is also not particularly limited. Examples of the composition component include, for example, DNA polymerase, nucleotide triphosphate, primer, solvent, etc. Further, as described above, it is preferable that albumin is added to the PCR reaction solution. In the PCR reaction solution, an order of adding the composition component is not limited at all.

The DNA polymerase is not particularly limited and polymerase derived from conventionally known thermoduric bacteria may be used, for example. Specifically, DNA polymerase derived from *Thermus aquaticus* (U.S. Pat. No. 4,889,818 and U.S. Pat. No. 5,079,352) Taq polymerase (trade name), DNA polymerase derived from *Thermus thermophilus* (WO91/09950) rTth DNA polymerase, DNA polymerase derived from *Pyrococcus furiosus* (WO92/9688) (Pfu DNA polymerase: manufactured by Stratagenes), DNA polymerase derived from *Thermococcus Storalis* (EP455-430(A)) Vent® (manufactured by Biolab New England), etc. are commercially available, and among which the DNA polymerase derived from *Thermus aquaticus* is preferable.

The ratio of the DNA polymerase in the reaction solution is not particularly limited however is, for example, in the range of 5 to 50 U/ml, preferably in the range of 1 to 100 U/ml, and more preferably in the range of 20 to 30 U/ml. With respect to DNA polymerase activity unit (U), generally, in an activity measurement reaction solution (25 mM TAPS buffer (pH 9.3, 25° C.), 60 mM KCl, 2 mM MgCl$_2$, 1 mM mercaptoethanol, 200 µM dATP, 200 µM dGTP, 200 µM dTTP, 100 µM [α-$^{32}$P] dCTP, and 0.25 mg/ml activated salmon sperm DNA), an activity that introduces 10 nmol of whole nucleotide into an acid-insoluble precipitate at 74° C. in 30 minutes is 1 U, wherein activated salmon sperm DNA is used as a template primer.

Normally, an example of the nucleotide triphosphate includes dNTP (dATP, dCTP, and dTTP). The ratio of dNTP in the reaction solution is not particularly limited however is, for example, in the range of 0.01 to 1 mmol/L, preferably in the range of 0.05 to 0.5 mmol/L, and more preferably in the range of 0.1 to 0.3 mmol/L.

The primer may be determined suitably according to a sequence or a length of the target nucleic acid. The length of the primer is normally in the range of about 10 to 50 bp. The ratio of the primer in the reaction solution is not particularly limited however is, for example, in the range of 0.01 to 5 µmol/L, preferably in the range of 0.1 to 3 µmol/L, and more preferably in the range of 0.1 to 1 µmol/L.

Examples of the solvent include buffer solution such as Tricine, MES, MOPS, HEPES, CAPS, etc. Commercially available PCR buffer solution, buffer solution of commercially available PCR kit, or the like may be used.

Further, the PCR reaction solution may include glycerol, heparin, betaine, etc. and the ratio thereof may be set in the range in which the PCR reaction is not hindered, for example.

Conditions of the cycle of PCR are not particularly limited however, for example, 1) dissociation of single-stranded DNA. 2) annealing of a primer, and 3) extension of the primer (a polymerase reaction) are as follows. Further, the number of the cycles is also not particularly limited however is, for example, preferably at least 30 cycles by assuming the following three steps of 1) to 3) as a cycle. The upper limit thereof is not particularly limited however is, for example, 100 cycles or less in total, preferably 70 cycles or less, further preferably 50 cycles or less. Temperature variation in each step may be controlled automatically with the thermal cycler, for example

TABLE 1

|  | | Temperature (° C.) | Time (second) |
|---|---|---|---|
| 1) Single-stranded DNA Dissociation | e.g. Preferably | 90-99 92-95 | 1-120 30-60 |
| 2) Primer Annealing | e.g. Preferably | 40-70 50-60 | 1-300 30-60 |
| 3) Extension Reaction | e.g. Preferably | 50-80 60-75 | 1-300 30-60 |

When the amplification product complementary to the target nucleic acid is produced in the aforementioned manner, the amplification product can be obtained that hardly is affected by the turbidity, the precipitate, or the like at the time of the detection by the optical unit.

Further, when the target nucleic acid in the whole blood sample is RNA (mRNA, total RNA), PCR may be carried out in the same manner as described above except that cDNA is prepared from the RNA by a reverse transcription reaction and the cDNA is used as the template of PCR (what is called reverse transcription PCR).

The reverse transcription reaction can be carried out, for example, by adding the whole blood sample to reverse transcription reaction solution containing conventionally known reverse transcription enzyme, the primer relative to the RNA, and nucleotide triphosphate (dNTP). The ratio of the whole blood sample in the reaction solution can be set, for example, to be the same as in the PCR reaction solution.

The reverse transcription reaction normally is carried out in advance of the PCR reaction. For example, the composition components of the PCR reaction solution may further be added to the reverse transcription reaction solution after the reverse transcription reaction. However, because the operation can be simplified and a risk of contamination can be reduced, it is preferable that the reverse transcription reaction and the PCR reaction are carried out continuously in one reaction system (what is called One-Step RT-PCR method)

Conditions of the reverse transcription reaction are not limited however are, for example, at 30 to 70° C. for 1 to 120 minutes, preferably at 40 to 60° C. for 10 to 60 minutes, and more preferably at 45 to 50° C. for 20 to 40 minutes.

[Amplification Product Analysis Method]

Next, as described above, a method of analyzing the amplification product of the present invention is a method of performing qualitative or quantitative analysis of the amplification product prepared by PCR, wherein the method includes:

(A) a process of preparing the amplification product complementary to the target nucleic acid in the whole blood sample by the method of producing the amplification product of the present invention; and (B) a process of detecting the amplification product by the optical means.

As described above, the method of analyzing of the present invention is characterized in that the ratio of the whole blood sample in the PCR reaction solution is set in the aforementioned ratio in the preparation process of the amplification product. Thereby, the effect of the precipitate, the turbidity, or the like can be suppressed and the detection of the amplification product by the optical unit can be carried out accurately. Therefore, in the method of analyzing of the present invention, as long as the ratio of the whole blood sample in the PCR reaction solution is in the aforementioned range, other conditions and processes are not limited at all.

A real time PCR method generally means a method of monitoring the preparation process of the amplification product with time in PCR. In the present invention, the aforementioned process (B), the process of detecting the amplification product by the optical unit, is referred to as real time PCR hereinafter. The detection of the amplification product in the process (B) may be carried out, for example, at the time of completion of the process (A) or after the completion of the process (A), that is, at the time of completion of the PCR reaction or after the completion of the PCR reaction, or the detection of the amplification product may be carried out concurrently with the process (A). When the detection of the amplification product is carried out concurrently with the process (A), the detection of the amplification product in the process (B) can be carried out with time, for example. Time lapse detection (monitoring) may be any one of continuous detection and discontinuous (intermittent) detection, for example. Further, the time lapse detection may be a monitoring only at a process of the PCR reaction in the process (A).

The amplification product prepared by the aforementioned method can be detected, for example, by measuring fluorescence intensity generated from the amplification product. A method of detecting the fluorescence is not particularly limited and includes conventionally known intercalator method, TaqMan® probe method, hybridization method, cycling probe method, etc.

The intercalator method is a method of using the intercalator that intercalates into the double-stranded DNA and produces the fluorescence when an excitation light is irradiated. In the case of adopting this method, for example, the fluorescence generated from the intercalator may be measured by preliminarily adding the intercalator to the PCR reaction solution and then irradiating the excitation light to the reaction solution (the intercalator in the reaction solution).

The TaqMan® probe method is a method of using a probe which has a partial sequence complementary to the template of PCR and includes a fluorescent substance and a quencher. An example of the probe includes oligonucleotide specifically annealed to a target sequence of the template, and the end portions thereof respectively are labeled with the fluorescent substance (5' end) and the quencher (3' end). The probe is not particularly limited however is preferably about 20 to 30 mer of oligonucleotide, for example. In the case of adopting this method, for example, the fluorescence generated from the fluorescent substance may be measured by preliminarily adding the probe to the PCR reaction solution and then irradiating the excitation light to the reaction solution (the fluorescent substance in the reaction solution). This method is based on the principle that, in the PCR reaction solution, the fluorescence of the fluorescent substance is inhibited due to the quencher even when the excitation light is irradiated if the probe is simply annealed to the template, however the probe is decomposed because of 5'→3' exonuclease activity of DNA polymerase when the DNA extension occurs in an extension process and the fluorescence is generated because of a disengagement of the fluorescent substance from the quencher.

The hybridization method is a method of using neighboring two kinds of probes that have a partial sequence complementary to the template of PCR. For example, the two kinds of probes are a combination of an oligonucleotide probe annealed at the 3' side of the template and 3' end of which is labeled with an acceptor fluorescent substance, and an oligonucleotide probe annealed at the 5' side of the template and 5' end of which is labeled with a donor fluorescent substance. In the case of adopting this method, for example, the fluorescence generated from the acceptor fluorescent substance may be measured by preliminarily adding the two kinds of probes to the PCR reaction solution and then irradiating the excitation light to the reaction solution (the acceptor fluorescent substance in the reaction solution). This method is based on the principle that, in the PCR reaction solution, the fluorescence is generated when the two kinds of probes are annealed to the template and the respective acceptor fluorescent substance and the donor fluorescent substance are neighboring, however the probe labeled with the acceptor fluorescent substance is decomposed when the DNA extension occurs in the extension process and the fluorescence is not generated because of a disengagement of the acceptor fluorescent substance from the donor fluorescent substance.

The cycling probe method is a method of using a probe that has a sequence complementary to the template of PCR and ends of which are labeled respectively with the fluorescent substance (5' end) and the quencher (3' end), and only center of which has a RNA sequence (a ribonucleotide sequence). In the case of adopting this method, for example, the fluorescence generated from the fluorescent substance may be measured by preliminarily adding the aforementioned probe and RNaseH to the PCR reaction solution and then irradiating the excitation light to the reaction solution (the fluorescent substance in the reaction solution). This method is based on the principle that, in the PCR reaction solution, the fluorescence of the fluorescent substance is inhibited due to the quencher even when the excitation light is irradiated if the probe simply is annealed to the template, however the fluorescence is generated because of a disengagement of the fluorescent substance at both ends from the quencher when a part of RNA forming chimeric duplex is cleaved by RNaseH, and the disconnection by the RNaseH does not occur if there is a mismatch in a RNA region.

The fluorescence intensity can be detected, for example, by a fluorometer. Generally, an apparatus comprising both a PCR reaction unit (e.g., thermal cycler) and an optical system unit (e.g., fluorometer) is used. Specific examples of which include commercially available Smart Cycler (trade name, manufactured by TAKARA BIO INC.), LightCycler (trade name, manufactured by Roche Diagnostics K. K.), and ABI PRISM 7000 (trade name, manufactured by Applied Biosystems).

In this manner, when the detection is carried out by the optical unit, for example, qualitative analysis (presence or absence of the amplification or the target nucleic acid) and quantitative analysis (the quantity of the amplification product) of the amplification product can be performed. In the a real time PCR, normally, an amplification curve to which the fluorescence intensity per cycle is plotted is created and the number of the cycles (Ct value: Threshold Cycle) in which the fluorescence intensity of the amplification product reach the set value (threshold value: e.g., the quantity in which the amplification is stopped) is analyzed. On the basis of the analysis content, qualitative or quantitative analysis of the amplification product and qualitative or quantitative analysis of the target nucleic acid contained in the whole blood sample can be performed. With respect to a method of setting the threshold value and performing quantitative analysis, a conventionally known method can be adopted. Further, after the completion of the PCR reaction, when the temperature of the reaction solution is increased and the melting temperature (Tm value) of the amplification product is detected (analyzed) by the optical unit, it can be confirmed whether the amplification product obtained is one kind or more than one kind, for example.

[Target Nucleic Acid Analysis Method]

Next, as described above, a method of analyzing the target nucleic acid is a method of performing quantitative analysis of the target nucleic acid contained in the sample, wherein the sample is the whole blood sample, and wherein the method includes:

(A) a process of preparing the amplification product complementary to the target nucleic acid in the whole blood sample by the method of producing the amplification product of the present invention;

(B) a process of performing quantitative analysis of the amplification product by detecting the amplification product by the optical unit; and (C) a process of performing quantitative analysis of the target nucleic acid contained in the whole blood sample that comprises confirming the number of the cycles of PCR where the amplification product reaches a specified quantity.

In the present invention, the aforementioned processes (A) and (B) are the method of analyzing the amplification product of the present invention described above. As described above, the present invention is characterized in that the whole blood sample in the PCR reaction solution is set in the aforementioned ratio in the process of preparing the amplification product. Thereby, the effect of the precipitate, the turbidity, or the like can be suppressed and the detection of the amplification product by the optical unit can accurately be carried out. As a result, the target nucleic acid can be analyzed accurately. Therefore, in the method of analyzing of the present invention, as long as the ratio of the whole blood sample in the PCR reaction solution is in the aforementioned range, other conditions and processes are not limited at all.

With respect to PCR, normally, when the amplification product reaches the certain quantity (threshold value), further amplification does not occur. Therefore, it is difficult to perform quantitative analysis of the target nucleic acid contained in the whole blood sample by simply measuring the quantity of the amplification product finally prepared. However, with the aforementioned real time PCR, since the preparation of the amplification product per cycle is monitored and the number of the cycles reaching the set threshold value (Ct value) is counted, for example, quantitative analysis of the target nucleic acid contained in the whole blood sample can be performed on the basis of the threshold value and the Ct value.

EXAMPLES

Next, examples of the present invention are described together with comparative examples. However, the present invention is not limited by the following examples and comparative examples.

Example 1

In this Example, PCR was carried out by setting the ratio of the whole blood sample in the PCR reaction solution at various values, and the Tm analysis of the obtained amplification product was carried out. A region of 408 bp out of β-globulin (human) was amplified by using forward primer GH20 (trade name, manufactured by TAKARA BIO INC.) and reverse primer GH21 (trade name, manufactured by TAKARA BIO INC.) represented by sequence Nos. 1 and 2 as the primers. Further, as the fluorescent substance for confirming the amplification of PCR, SYBER GREEN I (trade name), which is the intercalator, was used.

```
Sequence No. 1 (forward primer GH20)
5'-gaagagccaaggacaggtac-3'

Sequence No. 2 (reverse primer GH21)
5'-ggaaaatagaccaataggcag-3'
```

The whole blood of a healthy subject was added to the following PCR reaction solution in such a way that the ratio of the whole blood is at the predetermined ratio (0.02, 0.025, 0.033, 0.036, 0.038, 0.042, 0.045, 0.05, 0.0056, 0.0625, 0.071, 0.083, 0.1, 0.125, 0.17, 0.25, 0.29, 0.33, 0.4, 0.5, 0.67, 1, 2, 2.5, 3.3, 5, and 10% by volume). With respect to the PCR reaction solution, the PCR reaction was carried out with an amplification apparatus under the following conditions. Then, with respect to the reaction solution after the PCR reaction, the Tm analysis was carried out by measuring the fluorescence value (%) over the range of 515 to 555 nm. The conditions of the Tm analysis are as follows. In the meantime, PCR and the Tm analysis were carried out by using a combination of a thermal cycler, Eppendorf Master Cycler epS (trade name, manufactured by Eppendorf), and following optical system, Arkray system Ver.4 (trade name), as the amplification apparatus (same manner in other examples) (see WO2005/118772).

TABLE 2

(PCR Reaction Solution)

Taq buffer (trade name, manufactured by TAKARA BIO INC.)
0.2 mM dNTP (manufactured by TAKARA BIO INC.)
0.5 μM forward primer
0.5 μM reverse primer
25 U/ml Lr-Taq (manufactured by TAKARA BIO INC.)

TABLE 2-continued (PCR Reaction Solution)

| 1/5000 times diluted SYBER GREEN I |       |
| ---------------------------------- | ----- |
| Whole Blood Sample                 |       |
| Total                              | 50 μl |

TABLE 3

| | | Filter Range | |
| --- | --- | --- | --- |
| | LED | Light Emitting Side | Light Receiving Side |
| ch1 | 405 nm | 370-415 nm | 450-480 nm |
| ch2 | 470 nm | 420-485 nm | 515-555 nm |
| ch3 | 525 nm | 490-555 nm | 585-700 nm |

Light Emitting Element LED (manufactured by EPITEX INC.)
Light Receiving Element PD (model NO. 6931, manufactured by Hamamatsu photonics K.K.)

TABLE 4

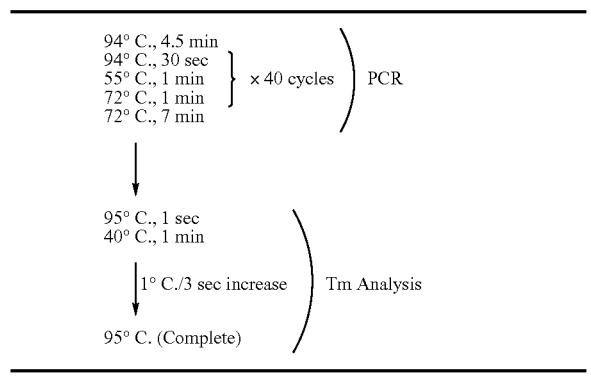

Results thereof are shown in FIG. 1. FIG. 1 is a graph indicating the relationships between the ratio of the whole blood sample in the PCR reaction solution and the fluorescence value. In FIG. 1, the vertical axis indicates the fluorescence value (%) and the horizontal axis indicates the ratio of the whole blood sample in the PCR reaction solution (final concentration: % by volume).

As shown in FIG. 1, when the ratio of the whole blood sample in the PCR reaction solution was at high concentration (especially, 2% or more than 2% by volume), the amplification of PCR could not be confirmed by a fluorescence measurement. This may be because the precipitate, the turbidity, or the like was generated in the reaction solution in the PCR reaction and the irradiated light was thereby blocked. In contrast, as shown in FIG. 1, the fluorescence measurement of the PCR amplification product could sufficiently be done by setting the ratio of the whole blood sample in the PCR reaction solution at 0.5% by volume or lower. This may be because the generation of the turbidity, or the like, could be suppressed while the PCR amplification efficiency was maintained sufficiently. These results show that, by setting the ratio of the whole blood sample in the aforementioned range, for example, qualitative or quantitative analysis of the target nucleic acid can be performed without pretreating the whole blood sample.

Example 2

Figure 2:
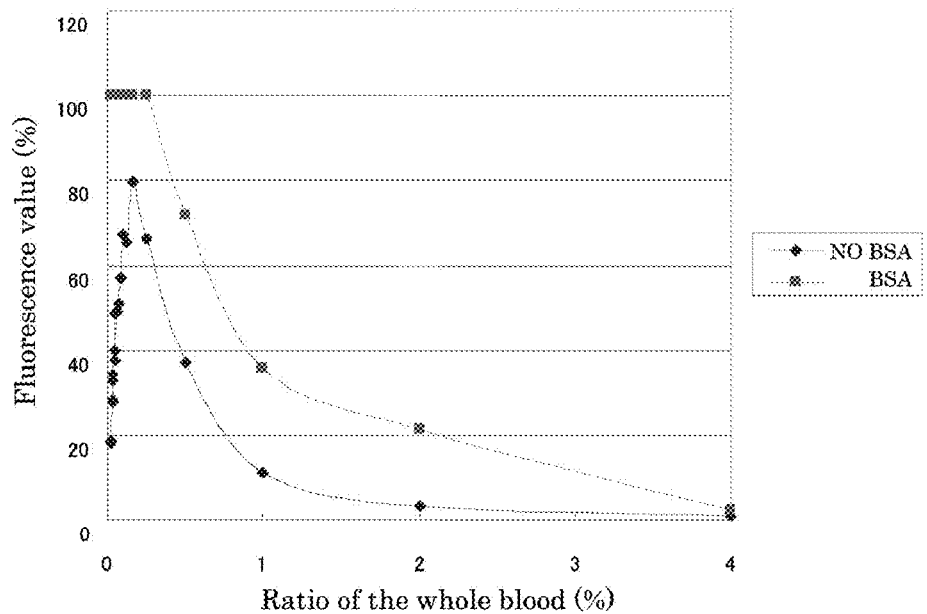
FIG. 2 is a graph indicating the relationships between a ratio of whole blood in a PCR reaction solution containing BSA and a fluorescence value corresponding to a PCR amplification product in an Example 2 of the present invention.

In this Example, BSA further was added to the PCR reaction solution, and the Tm analysis of the obtained amplification product was carried out. The Tm analysis of the amplification product was carried out in the same manner as in Example 1 except that 0.4% by weight of BSA was added, and a system without adding BSA also was measured in the same manner. Results thereof are shown in FIG. 2. FIG. 2 is a graph indicating the relationships between the ratio of the whole blood sample in the PCR reaction solution and the fluorescence value. In FIG. 2, ■ indicates the result in which BSA is added and ♦ indicates the result in which BSA is not added.

As shown in FIG. 2, by adding BSA to the PCR reaction solution, the fluorescence value was increased further compared with the results in which BSA was not added. Especially, with the sample in which the ratio of the blood (% by volume) in the PCR reaction solution was 0.5% by volume or lower, the fluorescence value was much further increased compared with the results in which BSA was not added. These results show that, in the PCR reaction solution, by adding BSA in addition to setting the ratio of the blood at 0.5% by volume or lower, the much further accurate fluorescence measurement of the PCR amplification product can be carried out.

Example 3

Figure 3:
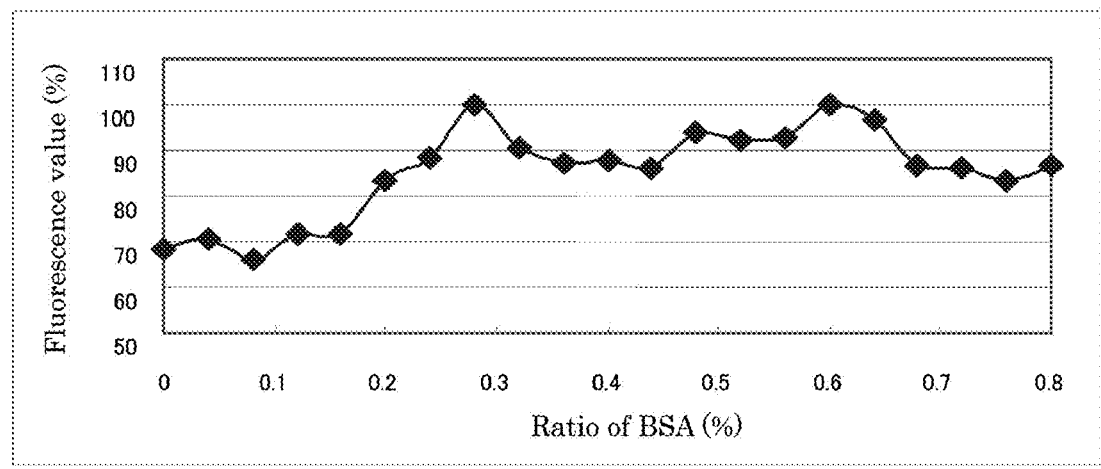
FIG. 3 is a graph indicating the relationships between a concentration of BSA in a reaction solution and a fluorescence value of the reaction solution in an Example 3 of the present invention.

An effect of the addition of BSA relative to the generation of the precipitate or the like due to the heating was confirmed. Since this effect was confirmed by an inhibition of the light in the fluorescence measurement, only the heat treatment was applied but no amplification reaction by PCR was carried out. Specifically, the whole blood and BSA were added to the reaction solution of the following component in such a manner that the ratio of the whole blood was at 0.4% by volume and the ratio of BSA was at the predetermined ratio (0, 0.04, 0.08, 0.12, 0.16, 0.2, 0.24, 0.28, 0.32, 0.36, 0.4, 0.44, 0.48, 0.52, 0.56, 0.6, 0.64, 0.68, 0.72, 0.76, and 0.8). Then, the reaction solution obtained was treated at 95° C. for 5 minutes with the same apparatus as in Example 1 and then the Tm analysis was carried out (measurement wave length 515-555 nm). Results thereof are shown in FIG. 3. FIG. 3 is a graph indicating the relationships between the ratio of BSA in the reaction solution and the fluorescence value.

TABLE 5

| Taq buffer (trade name, manufactured by TAKARA BIO INC.) | |
| --- | --- |
| Fluorescent Substance BODIPY FL (trade name, manufactured by Invitrogen) | |
| Whole Blood Sample | |
| Total | 50 μl |

As shown in FIG. 3, an increase in the fluorescence value was confirmed by adding BSA. Especially, by setting the ratio of BSA at 0.2% or more than 0.2% by volume, a remarkable increase in the fluorescence value was confirmed. This may be because the generation of the precipitate or the like was suppressed by adding BSA. These results show that, in the PCR reaction solution, by adding BSA (especially, 0.2% or more than 0.2% by volume) in addition to setting the ratio of the blood at 0.5% by volume or lower, the much further accurate fluorescence measurement of the PCR amplification product can be carried out.

Example 4

In this Example, the diluted whole blood sample was heated in advance of the PCR reaction, and PCR and the Tm analysis were carried out by setting the ratio of the whole blood in the PCR reaction solution at the predetermined ratio.

A region of 105 bp out of amylin gene was amplified by using a forward primer and a reverse primer represented by sequence Nos. 3 and 4 as the primers. Further, in order to confirm the amplification of PCR, the probe represented by sequence No. 5 was used.

```
Sequence No. 3 (forward primer)
5'-cacatgtgcaacgcagcg-3'

Sequence No. 4 (reverse primer)
5'-ctcttgccatatgtattggatccc-3'

Sequence No. 5 (detection probe)
5'-(FAM)-ttcattccagcaacaactttggtgccattctctc-
(DABCYL)-3'
```

10 μl of the whole blood of healthy subject obtained by using a heparin blood collecting tube was added to 90 μl of the following solution 1 for diluting a sample and mixed. 10 μl of the mixed solution was added to 90 μl of the following solution 2 for diluting a sample and mixed. The mixed solution thereby obtained was assumed as the diluted sample. Further, 10 μl of the diluted sample was heated at 95° C. for 6 minutes. Then, the real time PCR was carried out with the PCR reaction solution of the following component by using 10 μl of non-heated diluted sample or 10 μl of heated diluted sample. The analysis was carried out three times on the same sample (n=3).

[sample diluting solution 1: hereinafter, the same applies]
  10 mM Tris-HCl (pH8)
  0.1 mM EDTA
  0.05% NaN$_3$
  0.3% SDS

[sample diluting solution 2: hereinafter, the same applies]
  10 mM Tris-HCl (pH8)
  0.1 mM EDTA
  0.05% NaN$_3$

TABLE 6

| (PCR Reaction Solution: μl) | |
| --- | --- |
| Distilled Water | 30.4 |
| 20% BSA | 1 |
| 10× Gene Taq buffer* | 5 |
| 10 mM dAUGC | 1 |
| 100 mM MgCl$_2$ | 0.75 |
| 5 μM Detection Probe | 1 |
| 100 μM forward primer | 0.25 |
| 100 μM reverse primer | 0.25 |
| 2 U/μl UNG** | 0.1 |
| 5 U/μl Gene Taq NT* | 0.25 |
| Diluted Sample | 10 |
| Total | 50 μl |

*Gene Taq NT (trade name, manufactured by NIPPON GENE CO. LTD.)
**uracil-N-glycosylase Conditions of the real time PCR are as follows. The PCR reaction solution was treated at 50° C. for 2 minutes and at 95° C. for 2 minutes and then, by assuming the treatment at 95° C. for 15 seconds and at 56° C. for 45 seconds as a cycle, it was repeated for 50 cycles by i-Cycler (trade name, manufactured by BIO-RAD Laboratories, Inc.). At a step of 56° C. for 45 seconds of each cycle, the fluorescence of FAM in the detection probe was monitored with 530 nm wavelength.

Ct (threshold Cycle) values calculated by the i-Cycler are as follows. As described above, the Ct indicates the number of the cycles in which the fluorescence value correlated with the quantity of the amplification product reaches the set value (threshold value). The threshold value also was calculated by the i-Cycler and the threshold value of the fluorescence value in this Example was 184.2. In this state, from the principle of the real time PCR, it can be judged that an amount of an initial template is relatively large when the Ct value is relatively small.

TABLE 7

| | Ct Average Value | Ct |
| --- | --- | --- |
| Non-Heated | 33.9 | 34.7 |
| | | 33.7 |
| | | 33.3 |
| Heated | 32.2 | 32.1 |
| | | 31.9 |
| | | 32.7 |

Figure 4:
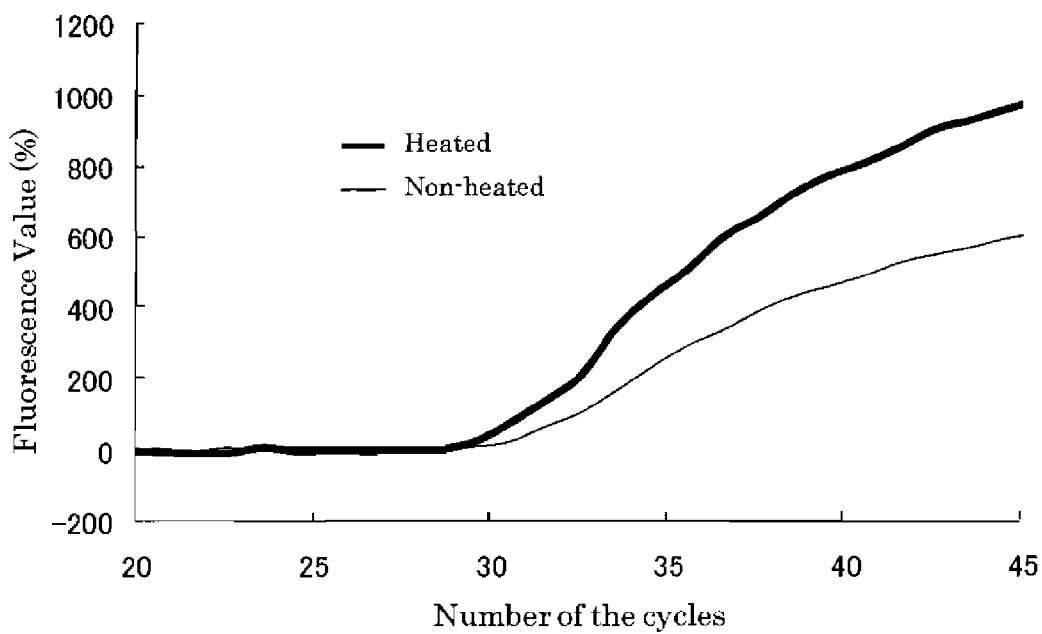
FIG. 4 is a graph indicating the relationships between the number of cycles of real time PCR and a fluorescence value for each sample in an Example 4 of the present invention.

With respect to the non-heated diluted sample and the heated diluted sample, average values of measurement values (n=3) thereof are respectively indicated in a graph in FIG. 4. FIG. 4 is a graph indicating the relationships between the number of the cycles and the fluorescence value for each sample. The thick line indicates the result of a heat treated diluted sample and the thin line indicates the result of an untreated diluted sample.

As shown in Table 7, by preliminarily applying the heat treatment to the diluted sample, the Ct value was reduced by 1.7 cycles on average compared with the non-heated diluted sample. This means that an amount of the initial template is 3.2 times greater by applying the heat treatment. Further, as shown in FIG. 4, in a graph form, the fluorescence value of the heat treated diluted sample clearly is increased from around 30$^{th}$ cycle compared with the non-heated diluted sample. From the Examples described above, it is found that the effect of the turbidity or the like can be suppressed while the PCR amplification efficiency is maintained sufficiently by setting the ratio of the whole blood sample in the PCR reaction solution in the predetermined range. Further, from this Example, it is found that the PCR amplification efficiency can further be increased by heating the diluted sample in advance of the PCR reaction.

Example 5

The real time PCR was carried out in the same manner as in Example 4 except that 10 μl of the whole blood of healthy subject obtained by using an EDTA blood collecting tube instead of the heparin blood collecting tube was used.

Figure 5:
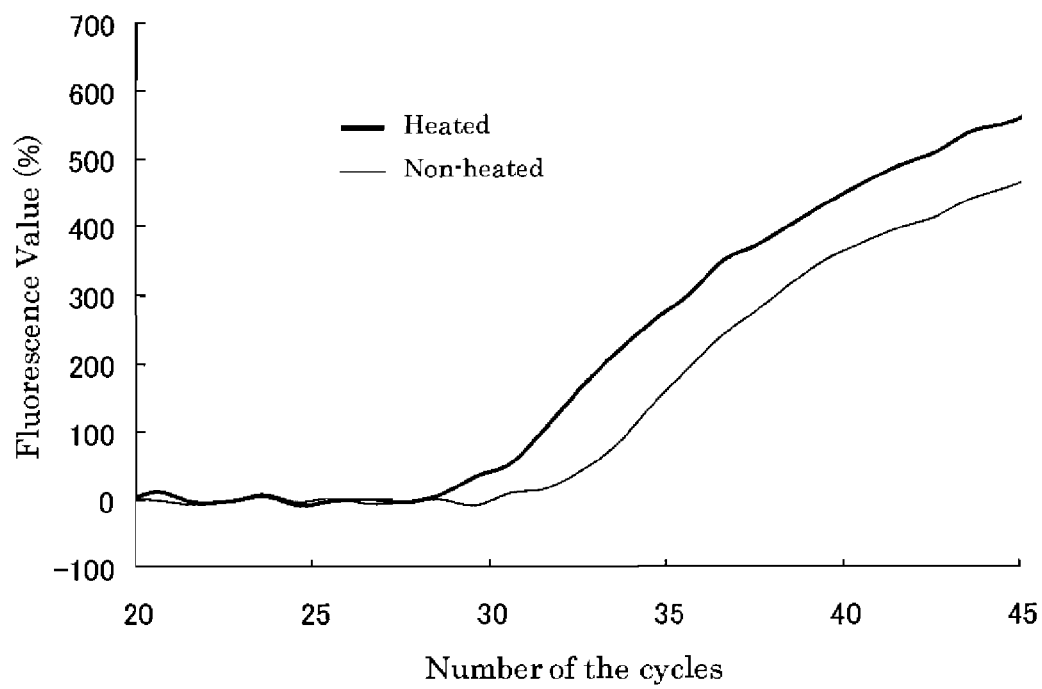
FIG. 5 is a graph indicating the relationships between the number of cycles of real time PCR and a fluorescence value for each sample in an Example 5 of the present invention.

The Ct value calculated by the i-Cycler is indicated in the following Table 8. Further, with respect to the non-heated diluted sample and the heated diluted sample, average values of the measurement values (n=3) are respectively indicated in a graph in FIG. 5. FIG. 5 is the graph indicating the relationships between the number of the cycles and the fluorescence value for each sample. The thick line indicates the result of the heat treated diluted sample and the thin line indicates the result of the untreated diluted sample.

TABLE 8

| | Ct Average Value | Ct |
| --- | --- | --- |
| Non-Heated | 35.4 | 35.8 |
| | | 35.4 |
| | | 35.1 |
| Heated | 33.0 | 33.6 |
| | | 32.9 |
| | | 32.6 |

As shown in Table 8, by preliminarily applying the heat treatment to the diluted sample, the Ct value was reduced by 2.4 cycles on average compared with the non-heated diluted sample. This means that the amount of the initial template is 5.3 times greater by applying the heat treatment. Further, as shown in FIG. 5, in a graph form, the fluorescence value of the heat treated diluted sample is clearly increased from around 30$^{th}$ cycle compared with the non-heated diluted sample. From the Examples described above, it is found that the effect of the turbidity or the like can be suppressed while the PCR amplification efficiency is sufficiently maintained by setting the ratio of the whole blood sample in the PCR reaction solution in the predetermined range. Further, from this Example, it is found that the PCR amplification efficiency further can be increased by heating the whole blood sample in advance of the PCR reaction.

Example 6

In this Example, the diluted whole blood sample was heated at the predetermined temperature in advance of the PCR reaction, and PCR and the Tm analysis were carried out by setting the ratio of the whole blood in the PCR reaction solution at the predetermined ratio.

As the primers, the forward primer and the reverse primer same as in Example 4 were used. Further, in order to confirm the amplification of PCR, the probe represented by sequence No. 6 was used.

Sequence No. 6 (Detection Probe)

5'-(FAM)-ttggtagatgagagaatggcaccaaagttgttgc-(DAB-CYL)-3'

10 µl of the whole blood of healthy subject obtained by using the EDTA blood collecting tube was added to 90 µl of the aforementioned solution 1 for diluting a sample and mixed. 10 µl of the mixed solution was added to 90 µl of the aforementioned solution 2 for diluting a sample and mixed. The mixed solution thereby obtained was assumed as the diluted sample. Further, 10 µl of the diluted sample was treated at the predetermined temperature (99° C., 95° C., 90° C., 85° C., and 80° C.) for 5 minutes. Then, the real time PCR was carried out with the PCR reaction solution of the following component by using 10 µl of the non-heated diluted sample or 10 µl of the heated diluted sample. Conditions of the real time PCR were as same as in Example 4.

TABLE 9

| (PCR Reaction Solution: µl) | |
|---|---|
| Distilled Water | 26.25 |
| 20% BSA | 0.5 |
| 10× Gene Taq buffer* | 5 |
| 10 mM dNTP | 4 |
| 100 mM MgCl$_2$ | 0.75 |
| 5 µM Detection Probe | 2 |
| 100 µM forward primer | 0.25 |
| 100 µM reverse primer | 0.25 |
| 5 U/µl Gene Taq NT* | 0.25 |
| Diluted Sample | 10 |
| Total | 50 µl |

*Gene Taq NT (trade name, manufactured by NIPPON GENE CO. LTD.)

The Ct values calculated by the i-Cycler are shown in the following table. The threshold value of the fluorescence value in this Example was 335.2.

TABLE 10

| | | Ct |
|---|---|---|
| Non-Heated | | 34.2 |
| Heated | 80° C. | 32.7 |
| | 85° C. | 32.8 |
| | 90° C. | 32.8 |
| | 95° C. | 32.6 |
| | 99° C. | 31.7 |

As shown in Table 10, when the diluted sample was preliminarily heated to 80 to 99° C., the difference between the Ct value of the heated diluted sample and that of the non-heated diluted sample was at least 0.6 cycles. At least 0.6 cycles means that the amount of the initial template is about 1.5 times greater. Accordingly, it is found that the PCR amplification efficiency can be increased further by applying the heat treatment to the diluted sample at least 80° C. It also is found that the amplification efficiency is relatively increased when the heating temperature is relatively high.

Example 7

In this Example, the diluted whole blood sample was heated at 80° or 99° C. in advance of the PCR reaction, and PCR and the Tm analysis were carried out by setting the ratio of the whole blood in the PCR reaction solution at the predetermined ratio.

The real time PCR was carried out in the same manner as in Example 6 except that the heating temperature was set at 80° C. or 99° C. and a heat treatment time was set at the predetermined time (30 seconds. 1 minute, 3 minutes, 10 minutes, and 15 minutes).

The Ct values calculated by the i-Cycler are shown in the following table. The threshold value of the fluorescence value in this Example was 165.4.

TABLE 11

| | | | Ct |
|---|---|---|---|
| Non-Heated | | | 35.7 |
| Heated | 80° C. | 30 seconds | 35 |
| | 80° C. | 1 minute | 35 |
| | 80° C. | 3 minutes | 34.7 |
| | 80° C. | 10 minutes | 33.5 |
| | 80° C. | 15 minutes | 33.2 |
| Heated | 99° C. | 30 seconds | 34.1 |
| | 99° C. | 1 minute | 32.2 |
| | 99° C. | 3 minutes | 31.9 |
| | 99° C. | 10 minutes | 31.5 |
| | 99° C. | 15 minutes | 31.6 |

As shown in Table 11, when the diluted sample preliminarily was heated at 80° C. or 99° C. for at least 30 seconds, the difference between the Ct value of the heated diluted sample and that of the non-heated diluted sample was at least 0.6 cycles. At least 0.6 cycles means that the amount of the initial template is about 1.5 times greater. Accordingly, it is found that the PCR amplification efficiency can be increased further by applying the heat treatment to the diluted sample at least 80° C. for at least 30 seconds.

INDUSTRIAL APPLICABILITY

As described above, according to the method of producing the amplification product of the present invention, only by setting the ratio of the whole blood sample in the PCR reaction solution in the aforementioned range, the effect of the turbidity, the precipitate, or the like on the detection can be suppressed without applying the pretreatment of the whole blood sample or aftertreatment of the PCR reaction solution as conventional. Further, because the effect of the turbidity, the precipitate, or the like on the detection can be suppressed, the detection of the amplification product can be carried out not only by electrophoresis as conventional but also by the optical unit. Moreover, because the detection by the optical unit can be done, for example, the monitoring of the amplification product in the preparation process with time can be realized which is impossible by electrophoresis. Therefore, according to the present invention, even when the whole blood sample is used, for example, not only qualitative or quantitative analysis of the amplification product but also qualitative or quantitative analysis of the target nucleic acid can be performed.

The invention claimed is:

1. A method of analyzing an amplification product; performing qualitative or quantitative analysis of the amplification product prepared by PCR, wherein the method includes:
   (A) preparing the amplification product complementary to a target nucleic acid in a whole blood sample by PCR, wherein a ratio of the whole blood sample in a PCR reaction solution is in a range of 0.01 to 0.9% by volume; and
   (B) detecting the amplification product by an optical unit.

2. The method of analyzing an amplification product according to claim 1, wherein albumin is added to the PCR reaction solution in advance of start of PCR reaction.

3. The method of analyzing an amplification product according to claim 2, wherein a ratio of albumin in the PCR reaction solution is in a range of 0.1 to 1% by weight.

4. The method of analyzing an amplification product according to claim 2, wherein albumin is at least one selected from a group consisting of bovine serum albumin, human serum albumin, rat serum albumin, and horse serum albumin.

5. The method of analyzing an amplification product according to claim 1, further comprising applying a heat treatment to the whole blood sample in advance of start of PCR reaction.

6. The method of analyzing an amplification product according to claim 5, wherein
   the heat treatment is applied to a diluted sample of the whole blood sample in the process of the heat treatment, and
   a ratio of the whole blood sample in the diluted sample is in a range of 0.01 to 90% by volume.

7. The method of analyzing an amplification product according to claim 5, wherein a heating temperature in the process of the heat treatment is in a range of 80 to 99° C.

8. The method of analyzing an amplification product according to claim 5, wherein a treating time in the process of the heat treatment is at least 30 seconds.

9. The method of analyzing an amplification product according to claim 1, wherein the target nucleic acid in the whole blood sample is DNA and the DNA is a template of PCR.

10. The method of analyzing an amplification product according to claim 1, wherein
    the target nucleic acid in the whole blood sample is RNA, and
    cDNA prepared from the RNA by a reverse transcription reaction is a template of PCR.

11. The method of analyzing an amplification product according to claim 1, wherein the number of amplifications of PCR is at least 30 cycles.

12. The method of analyzing the amplification product according to claim 1, wherein the amplification product is detected with time in the process (B).

13. The method of analyzing the amplification product according to claim 1, wherein the amplification product is detected by measuring a fluorescence generated from the amplification product.

14. The method of analyzing the amplification product according to claim 1, wherein the optical unit is a fluorometer.

15. The method of analyzing the amplification product according to claim 1, wherein the PCR reaction solution further contains intercalator which intercalates into double-stranded DNA, and in the process (B), the amplification product is detected by measuring a fluorescence generated in response to an irradiation of an excitation light to the intercalator.

16. The method of analyzing the amplification product according to claim 1, wherein the PCR reaction solution further contains fluorescent substance, quencher, and a probe having a partial sequence complementary to a template of PCR, and
    in the process (B), the amplification product is detected by measuring a fluorescence generated in response to an irradiation of an excitation light to the fluorescent substance.

17. The method of analyzing the amplification product according to claim 1, wherein, in the process (B), the method of detecting the amplification product is a Tm analysis.

18. A method of analyzing a target nucleic acid; performing quantitative analysis of the target nucleic acid contained in a sample, wherein the sample is a whole blood sample, and wherein the method includes:
    (A) preparing an amplification product complementary to the target nucleic acid in the whole blood sample by PCR,
    wherein a ratio of the whole blood sample in a PCR reaction solution is in a range of 0.01 to 0.9% by volume;
    (B) performing quantitative analysis of the amplification product by detecting the amplification product by an optical unit; and
    (C) performing quantitative analysis of the target nucleic acid contained in the whole blood sample that comprises confirming the number of cycles of PCR where the amplification product reaches a specified quantity.

19. The method of analyzing the target nucleic acid according to claim 18, wherein, in the process (B), the amplification product is detected with time.

20. The method of analyzing the target nucleic acid according to claim 18, wherein the amplification product is detected by measuring a fluorescence generated from the amplification product.

21. The method of analyzing the target nucleic acid according to claim 18, wherein the optical unit is a fluorometer.

22. The method of analyzing the target nucleic acid according to claim 18, wherein, in the process (B), the method of detecting the amplification product is a Tm analysis.

23. A method of suppressing the effect of precipitate and/or turbidity in PCR amplification of a whole blood sample, the method comprising:
    preparing an amplification product complementary to a target nucleic acid in the whole blood sample by PCR, and
    limiting a ratio of the whole blood sample in a PCR reaction solution to be in a range of 0.01 to 0.9% by volume.

24. The method of analyzing the amplification product according to claim 1, wherein the ratio of the whole blood sample in the PCR reaction solution is in a range of 0.01 to 1.8 g/L in term of hemoglobin content.

25. The method of analyzing the target nucleic acid according to claim 18, wherein the ratio of the whole blood sample in the PCR reaction solution is in a range of 0.01 to 1.8 g/L in term of hemoglobin content.

26. The method of suppressing the effect of precipitate and/or turbidity in PCR amplification of a whole blood sample according to claim 23, further comprising limiting a ratio of the whole blood sample in the PCR reaction solution to be in a range of 0.01 to 1.8 g/L in term of hemoglobin content.

* * * * *